United States Patent [19]

Stacpoole et al.

[11] Patent Number: 4,801,597

[45] Date of Patent: Jan. 31, 1989

[54] CERTAIN INOSITOL-NICOTINATE ESTER DERIVATIVES AND POLYIONIC COMPLEXES THEREFORE USEFUL FOR TREATING DIABETES MEUITUS, HYPERLIPIDEMIA AND LACTIC ACIDOSIS

[75] Inventors: Peter W. Stacpoole; Nicholas S. Bodor, both of Gainesville, Fla.

[73] Assignee: University of Florida, Gainesville, Fla.

[21] Appl. No.: 743,396

[22] Filed: Jun. 11, 1985

[51] Int. Cl.$^4$ .................... C07D 401/12; A61K 31/44
[52] U.S. Cl. .................................. 514/332; 546/263; 546/318
[58] Field of Search ................. 546/263, 318; 514/332

[56] References Cited

U.S. PATENT DOCUMENTS 4,558,050 12/1985 Stacpoole ........................... 514/252

OTHER PUBLICATIONS

Bodor, Chemical abstracts, vol. 105(16), abst. No. 139,615j, Oct. 20, 1986.

Primary Examiner—Alan L. Rotman
Attorney, Agent, or Firm—Dennis P. Clarke

[57] ABSTRACT

The present invention relates to pharmaceutical compositions and methods for the treatment of metabolic disorders and to certain inositol-nicotinate dichloroacetate derivatives as the active ingredients therein.

11 Claims, 1 Drawing Sheet

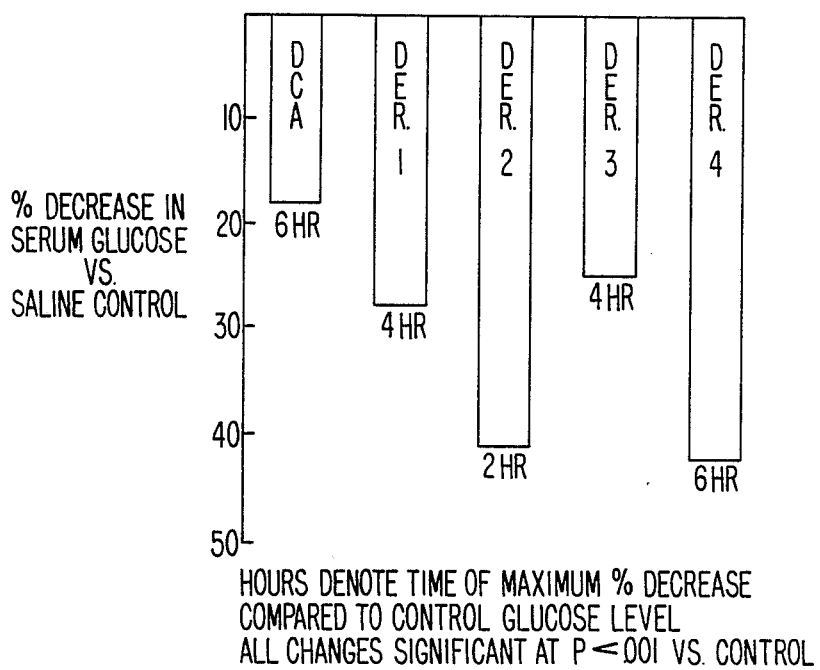
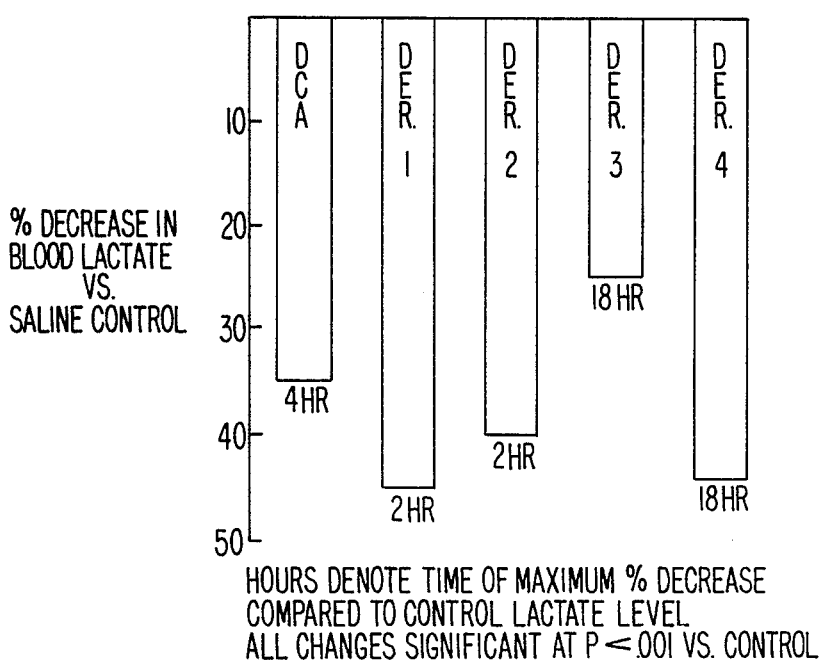

4,801,597

CERTAIN INOSITOL-NICOTINATE ESTER DERIVATIVES AND POLYIONIC COMPLEXES THEREFORE USEFUL FOR TREATING DIABETES MEUTUS, HYPERLIPIDEMIA AND LACTIC ACIDOSIS

BACKGROUND OF INVENTION

Related Applications

The invention described herein is related to that disclosed in U.S. application Ser. No. 584,994 filed Mar. 1, 1984, now U.S. Pat. No. 4,558,050 issued Dec. 10, 1985.

PRIOR ART

The pharmacologic and therapeutic properties of salts of dichloroacetic acid (DCA) have been extensively studied over the last several years. Researchers have found that DCA stimulates glucose uptake and utilization by peripheral tissues [Stacpoole et al, Metabolism, 19:71 (1970); McAllister et al, Biochem. J. 134:1067 (1973); Diamond et al, Diabetes 31:326 (1982)] and inhibits hepatic glucose production [Stacpoole, Metabolism 26:107 (1977); Demangre et al, Biochem. J. 172:91 (1978); Diamond et al, Metabolism 30:880 (1981)]. It has also been found to decrease blood glucose levels in patients with diabetes mellitus [Stacpoole et al, N. Eng. J. Med. 298:526 (1978)]. DCA also stimulates lactate oxidation in animal tissues and significantly decreases lactic acid levels and overall morbidity in patients with lactic acidosis [Stacpoole et al, N. Engl. J. Med. 309:390 (1983); Blackshear et al, Diabetes Care 5:391 (1982)]. In addition, DCA reduces circulating triglyceride and cholesterol concentrations in obese [Felts et al, Diabetes, 25 (suppl.):363 (1976)] and diabetic [Hayet et al, Metabolism 29:120 (1980); Riles et al, Diabetes 28:852 (1979)] animals. DCA also markedly decreases blood cholesterol levels in patients with various forms of hyperlipidemia [Stacpoole et al, N. Eng. J. Med., 298:526 (1978); Moore et al, Atherosclerosis 33:285 (1979)].

The efficacy of DCA for the treatment of metabolic disorders, however, is compromised by the fact that DCA is toxic to lower animals and humans, particularly upon chronic administration. It has been reported that a human patient who received DCA for about four months developed a mild polyneuropathy that resolved when treatment stopped [Moore et al, ibid.] Chronic administration of DCA to lower animals in doses exceeding those used clinically also induces a reversible peripheral neuropathy, changes in testicular morphology and lenticular opacities [Stacpoole, N. Eng. J. Med. 300:372 (1979)].

DCA is known to oxidize in vivo to glyoxylate and subsequently to oxalate [Demangre et al, Biochem. Biophys. Res. Comm. 85:1180 (1978); Harris et al, Arch. Biochem. Biophys. 189:364 (1978) and Currey et al, Clin. Pharmacol. Ther., Vol. 37:894 (1985)]. Oxalate is a known neurotoxin [Bilbao et al, Can. J. Neurol. Sci. 3:63 (1976)] and cataract inducing chemical "Fielder et al, Br. J. Ophthal.. 64:782 (1980)], and may be at least partly responsible for the neuropathic changes associated with the chronic administration of DCA.

It is an object of the present invention to ameliorate the toxicity associated with DCA and provide compounds, compositions and methods for the safe and effective treatment of certain metabolic disorders.

SUMMARY OF THE INVENTION

One embodiment of the invention comprises esters of dichloroacetic acid having the formula:

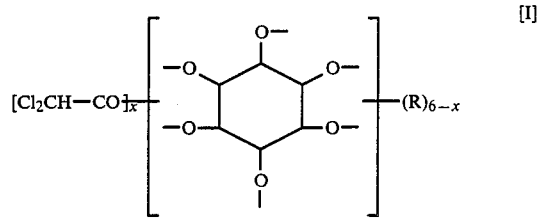

Wherein:
R is H,

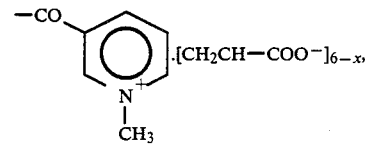

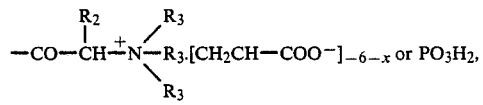

x is an integer from 1 to 6,
$R_2$ is H, alkyl or the residue of a naturally occuring amino acid, and
$R_3$ is lower alkyl; or

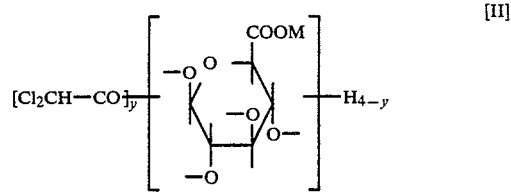

Wherein:
y is an integer from 1 to 4, and
M is a monovalent metal ion;
or a pharmaceutically acceptable derivative thereof.

A further embodiment of the invention comprises dichloroacetate polyionic complexes having the formula:

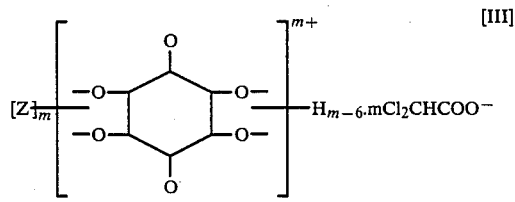

Wherein:
Z is

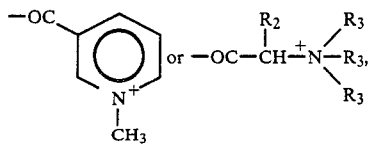

M is an integer from 1 to 6,
R₂ has the meanings set forth above,
R₃ is lower alkyl;
or a pharmaceutically acceptable derivative thereof.

It will be understood that in the above structural formulae I and III, R₂ may be, in addition to the specified groups, the residue of an acid such that the group

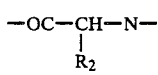

is the acyl radical of a naturally occurring amino acid, e.g., glycine, alamine, phenylalamine, etc.

It will further be understood that R₃ may be any lower alkyl group having from 1 to 4 carbon atoms.

The invention further provides pharmaceutical compositions in unit dosage form adapted for administration to a lower animal or human for the treatment of a metabolic disease comprising [a] a therapeutically effective amount of (1) an ester of formula I or II, or (2) a complex of formula III and [b] a pharmaceutically acceptable carrier therefor.

Finally, the invention provides methods for the treatment of metabolic diseases comprising administering to a lower animal or human in need thereof a therapeutically effective amount of (1) the ester of formula I or II, or (2) the complex of formula III.

DETAILED DESCRIPTION OF THE INVENTION

Dichloroacetic acid and salts thereof are referred to herein as "DCA".

The present invention is predicated on the discovery that certain derivatives of DCA retain the biochemical properties of DCA while minimizing or eliminating the toxic characteristics thereof. While not wishing to be bound by any theory as to the mechanism of the invention, it is hypothesized that the above esters and complexes possess slower rates of in vivo metabolism to glyoxalates and oxalates and act to release DCA in a sustained manner when administered. It is believed that this combination of slower metabolic decomposition and sustained release effectively ameliorates the toxicity of DCA while retaining the desired biologic properties thereof.

It will be understood by those skilled in the art that not all derivatives of DCA will possess an appropriate rate of metabolic decomposition to DCA.

Of the esters of formula I, the preferred esters are those of formula I wherein R is H or those wherein x is 4 or 6. Particularly preferred is the ester of formula I wherein x is 6. Also particularly preferred are those esters of formula I wherein x is 4 and, of the remaining R groups, one R is H and the other is —PO₃H₂. Of these latter, a particularly preferred ester is that of the formula:

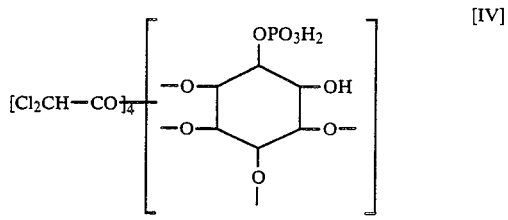

Of the esters of Formula II, the preferred esters are those of Formula II wherein y is 4. A particularly preferred ester is that of formula II wherein y is 4 and M is potassium.

Of the esters of formula III, the preferred esters are those of the formula wherein Z is

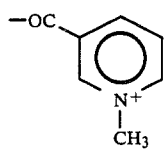

A particularly preferred ester is that of formula III wherein Z is the N-methyl nicotinate group depicted above and m is 6.

The derivatives have been found to be particularly effective for the treatment of diabetes mellitus, hyperlipidemia (hypercholesterolemia, hypertriglycidemia, or both) and lactic acidosis. It will be understood, however, by those skilled in the art that the esters, complexes, compositions and methods of the invention are applicable for the treatment of any metabolic disorder or disease against which DCA alone is effective.

It is preferred to formulate the above dichloroacetate derivatives with pharmaceutically acceptable carriers adapted for oral administration (i.e., tablet, capsule or pill) and to administer the derivatives orally. It wil be understood by those skilled in the art, however, that the active agent may also be compounded for parenteral or transdermal administration. The active ingredient may be admixed or compounded with any conventional, pharmaceutically acceptable carrier. It will be understood by those skilled in the art that any mode of administration, vehicle or carrier heretofore employed for the administration of DCA alone may be utilized for preparing and administering the pharmaceutical compositions of the present invention. Illustrative of such methods, vehicles and carriers are those described by Stacpoole et al [N. Eng. J. Med., 309:390 (1983) and N. Eng. J. Med., 298:526 (1978)], the disclosures of which are incorporated herein by reference. Those skilled in the art, having been exposed to the principles of the invention will experience no difficulty in determining suitable and appropriate vehicles, excipients and carriers or in compounding the active ingredients therewith to form the pharmaceutical compositions of the invention.

The therapeutically effective amount of DCA derivative to be included in the pharmaceutical composition of the invention depends, in each case, upon several factors, e.g., the type, size and condition of the animal, the metabolic disorder to be treated, the intended mode of administration, the capacity of the animal to incorporate the intended dosage form, etc. Generally, an amount of DCA compound is included in each dosage form to provide an amount of DCA employed in conventional pharmaceutical compositions containing DCA alone (Cf. Stacpoole et al, supra), i.e., from about 100 to about 10,000 mg, preferably about 100 to about 5,000 mg.

The dichloroacetate acid-thiamine compound or the mixture of DCA and thiamine may be solubilized in a suitable solvent, e.g., water, ethanol, etc. and lyophilized for later reconstitution with the above-noted carrier media for parenteral, oral or transdermal administration.

Those skilled in the art will be aware that the amounts of the various components of the compositions of the invention to be administered in accordance with the method of the invention to a patient will depend upon those factors noted above.

Generally, however, amounts of the derivative are administered to provide dosages of DCA moeity conventionally employed in the treatment of metabolic disorders, i.e., from about 1 to about 100 mg/kg, preferably from about 10 to about 50 mg/kg of the DCA moiety, the frequency of administration and duration of treatment being dependent upon the type and nature of the animal and metabolic disorder treated.

The invention is illustrated by the following non-limiting examples.

EXAMPLE 1

Preparation of Inositol-Hexa(N-methylnicotinate-dichloroacetate)

(a) Preparation of Inositol-Hexanicotinate

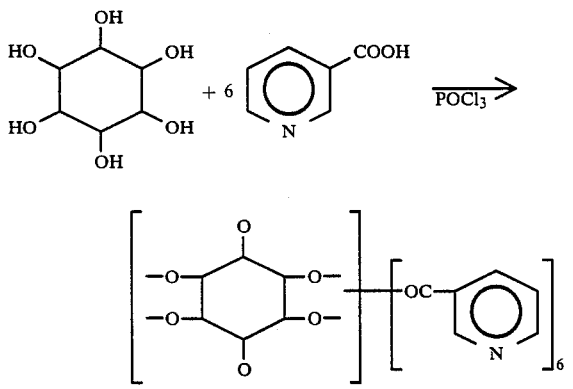

To a suspension of 25 g (0.204M) of nicotinic acid in 67.5 ml (0.85M) pyridine was added 17 g (0.11M) of $POCl_3$. The temperature was kept at about 60° C. for one hour while the mixture was stirred (it turned darker after adding $POCl_3$). After one hour 6.2 g (0.03M) of inositol was added and the temperature of the mixture was kept at about 80° C. while stirring for another three hours. Then the reaction mixture was poured into 100 ml of ice-water and yellowish solids were separated from brown mother liquor by filtration. Solids were washed with ice-water, acetone and then dried overnight at t=110° C. 23.5 g of product was obtained (yield 85.7%). M.P. 253°–255° C. NMR was consistent with the desired product. Crystallization from Chloroform/ether gave white crystals.

Microanalysis for $C_{42}H_{30}N_6O_{12}$

|  | C | H |
|---|---|---|
| Calc: | 62.23; | 3.70 |
| Found: | 61.94; | 3.71; |

(b) Preparation of Inositol-Hexa(N-methylnicotinate-iodide)

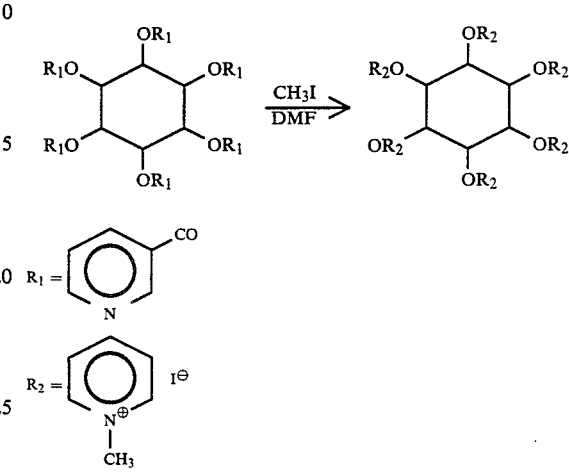

3 g (3.7 mM) of inositol hexanicotinate was dissolved (temperature about 55° C.) in 300 ml of DMF; after cooling 3.3 g (23 mM) of methyl-iodide was added. The reaction mixture was left under reflux of $CH_3I$ (bath temperature 50°–55° C.) for 50 hours, while stirring. Yellow precipitates came out. These solids were separated by filtration, washed with acetone and dried (90° C.) for 3 hours. Yield 2.95 g (48.0%) M.P. 265°–7° C. (decomp.) NMR showed desired product.

(c) Exchange of I-anion for $CCl_2HCOO$ anion on Inositol-Hexa (n-methyl-nicotinate-iodide)

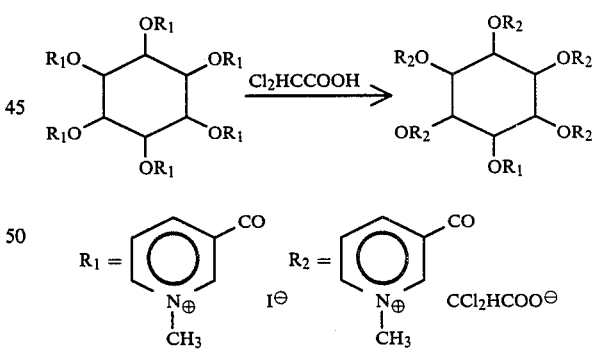

Exchange of ions was effected on a carboxylic column, Amberlite IRC-50. 0.5 g (0.32 mM) of iodide was dissolved in 10 mL of water. This solution was slowly run through the column, then the column was washed with water and outlet solution was checked for $I^-$ with $AgNO_3$. When no more I anions were detected, the outlet water solution was collected (about 150 mL) and 2 ml of 1N $Cl_2HCCOOH$ were added to it. This solution was stirred overnight, then condensed in vacuum, and triturated with Et. ether. 0.15 g (yield 30%) of yellowish solids were obtained. M.P. 140°–143° C. NMR showed desired product.

Microanalysis for $C_{60}H_{54}O_{24}N_6Cl_{12} \times 6H_2O$

| | C | H | N | Cl |
|---|---|---|---|---|
| Calcd. | 40.56; | 3.74 | 4.73; | 23.95 |
| Found: | 40.69; | 3.69; | 4.74; | 24.05. |

EXAMPLE 2

Preparation of Dichloroacetate of Glucuronic Acid

R = Cl$_2$HCCO 5 g (0.026M) of dry glucuronic acid and 1.27 g (0.0104M) of catalyst (4-dimethylaminopyridine) were dissolved in 30 ml of warm DMF. After cooling this solution on an ice-bath, 15.3 g (0.104M) of dichloroacetylchloride was slowly added to the solution. When the ice melted the reaction mixture was stirred at room temperature for 5 hours. After dilution of the reaction mixture R.M. with 100 ml of Et. ether, it was washed three times with 100 ml of water. The ether solution was dried over MgSO$_4$ and condensed in vacuo (max temperature 50° C.). 11.6 g of yellow oil (yield 70.6%) was obtained. NMR was consistent with the desired product.

Microanalysis for 1:1 mixture of tetraester C$_{14}$H$_{10}$O$_{11}$Cl$_8$ and tri-ester C$_{12}$H$_{10}$O$_{10}$Cl$_6$

| | C | H | Cl |
|---|---|---|---|
| Calcd: | 26.85; | 1.75; | 42.35 |
| Found: | 26.78; | 2.06; | 42.81. |

EXAMPLE 3

Preparation of Potassium Salt of Glucuronic Acid-dichloroacetate

A saturated methanol solution of KOH was added to 3 g (4.7M) of the dichloroacetylated glucuronic acid product of Example 2 during stirring and cooling on ice-bath. When the pH exceeded 10, beige crystals started to precipitate. The crystals were separated by filtration, recrystallized in methanol and dried. 2 g (63% yield) of salt was obtained. NMR was consistent with the desired product.

EXAMPLE 4

Preparation of Hexa-dichloroacetyl-inositol

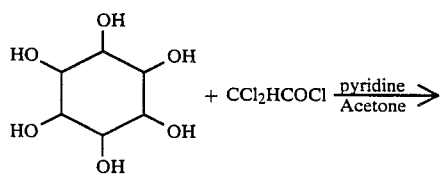

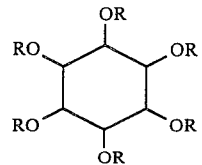

R = Cl$_2$HCCO

The mixture of 4.5 g (0.025M) dry inositol and 33.5 g (0.225M) of dichloroacetylchloride was stirred at room temperature for one hour, then 50 ml of dry acetone was added. The reaction mixture was cooled down on an ice-bath and 17.8 g (0.225M) of dry pyridine was very slowly added dropwise to the reaction mixture. After adding all of the pyridine the reaction mixture was stirred at room temperature for 17 hours. After evaporation to dryness under reduced pressure the mixture was extracted with 200 ml of hot ethylacetate and the solution was washed with water, 5% potassium carbonate and, finally water. After drying over anhydrous sodium sulfate the solvent was removed in vacuo. The residue oil was crystallized from chloroform during freezing and yellow crystals recrystallized from mixture CHCl$_3$/ether. NMR was consistent with the desired product.

Microanalysis for C$_{18}$H$_{12}$O$_{12}$Cl$_{12}$

| | C | H |
|---|---|---|
| Calcd: | 25.72; | 1.59 |
| Found: | 25.53; | 1.42. |

EXAMPLE 5

Preparation of Inositol-monophosphate

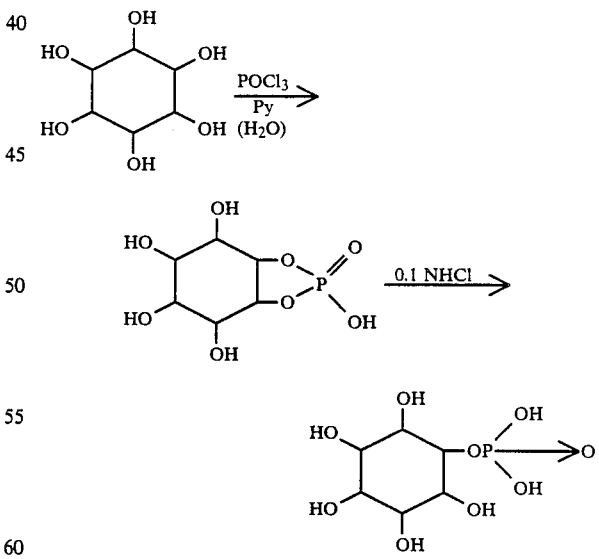

To 6 g (33 mM) of inositol in 300 ml of pyridine was slowly added at room temperature 10.25 g (66 mM) of phosphoryl chloride in 30 ml of pyridine. When all the POCl$_3$ was introduced, 1 ml of water was slowly added and reaction mixture was stirred for ½ hour at room temperature. The precipitate was separated by filtration and dried. There were obtained 13.2 g of product.

The precipitate obtained was dissolved in 600 ml of 0.1 NHCl during heating. The solution was stirred at 95°–100° C. for 1 hour, then it was condensed in vacuo. The product was precipitated with ether. 4.8 g of white crystals were obtained (yield 55.4%) M.P. 102°–103° C.

EXAMPLE 6

Preparation of Inositol-monophosphate-tetra-dichloroacetate

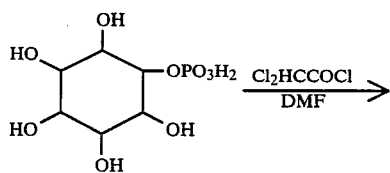

R = Cl₂HCCO

To 0.95 g (7.5 mM) of inositol monophosphate in 50 ml of DMF were slowly added during cooling 11.1 g (74 mM) of dichloroacetyl chloride. The reaction mixture was stirred at room temperature for 24 hours, then condensed in vacuo; 3.67 g yellowish crystals were obtained (70% yield). After recrystallization from MeOH+EtOH (2:1) white crystals were obtained. The NMR was consistent with the desired product.

EXAMPLE 7

The biological activity was determined for four derivatives: potassium tetra(dichloroacetyl)glucuronate (Derivative 1), inositol monophosphatetetradichloroacetate (Derivative 2), inositol hexadichloroacetate (Derivative 3) and inositol hexa(N-methylnicotinate-dichloroacetate) (Derivative 4). Rats fasted for 24 hours received single, orogastric doses of saline (control), sodium DCA (100 mg/kg) or each derivative at a dose providing an equivalent 100 mg/kg dose of DCA. Changes in serum glucose and blood lactate were monitored over 24 hours. Results are expressed as (1) maximum percent decrease in glucose or lactace, relative to control, (2) the time at which the maximum changes occurred, and (3) the duration of action of the drug.

FIG. 1 shows that all of the compounds tested decreased serum glucose levels, with maxima ranging between 18% and 24%. All derivatives were more potent than DCA. The timing of the peak effect varied from 2 hours to 6 hours. The duration of action was as follows:

| DCA: | 17 hours |
|---|---|
| Derivative 1: | >24 hours |
| Derivative 2: | 24 hours |
| Derivative 3: | 6 hours |
| Derivative 4: | >24 hours |

FIG. 2 reveals these compounds were also active in markedly decreasing blood lactate concentrations. Only derivative 3 was less potent than DCA. The timing of the maximal effect ranged between 2 hours and 18 hours. The duration of action was as follows:

| DCA: | 18 hours |
|---|---|
| Derivative 1: | >24 hours |
| Derivative 2: | >24 hours |
| Derivative 3: | 8 hours |
| Derivative 4: | >24 hours |

These results indicate that the derivatives tested have different pharmacokinetics and bioavailability than the parent molecule, DCA. Furthermore, the comparative pharmacokinetic investigations with DCA and Derivative 4 show that the formation of oxalate from the derivatives of the invention is minimal and unlikely to be toxic.

We claim:

1. A dichloroacetate polyionic complex having the formula:

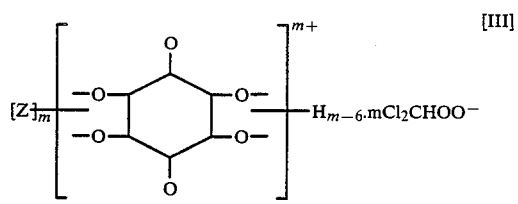

Wherein:
Z is

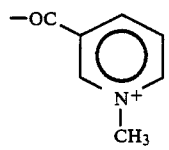

and m is an integer from 1 to 6.

2. A complex of claim 1 wherein Z is

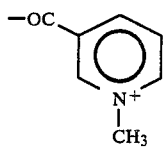

3. A complex of claim 2 wherein m is 6.

4. An ester of dichloracetic acid having the formula:

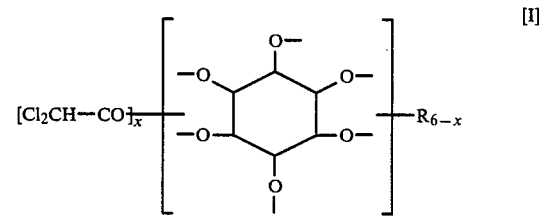

Wherein:
R is

11

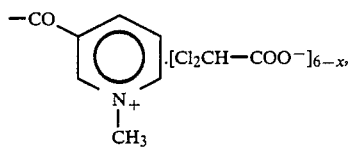

and x is an integer from 1 to 6.

5. An ester of claim 4 wherein R is

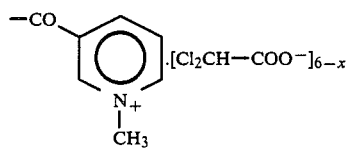

6. A pharmaceutical composition in unit dosage form adapted for administration to a human for the treatment of diabetes mellitus, hyperlipidemia, or lactic acidosis comprising a therapeutically effective amount of the ester of claim 4 pharmaceutically acceptable carrier therefor.

7. The composition of claim 6 adapted for oral administration to said human.

8. A method for the treatment of diabetes mellitus, hyperlipidemia, or lactic acidosis comprising administering to a human in need thereof a therapeutically effective amount of the ester of claim 4.

9. The method of claim 8 comprising orally administering said ester or complex to said human.

10. A pharmaceutical composition in unit dosage form adapted for administration to a human for the treatment of diabetes mellitus, hyperlipidemia, or lactic acidosis comprising a therapeutically effective amount of the polyionic complex of claim 1 in admixture with a pharmaceutically acceptable carrier therefor.

11. A method for the treatment of diabetes mellitus, hyperlipidemia, or lactic acidosis comprising administering to a human in need thereof a therapeutically effective amount of the polyionic complex of claim 1.

* * * * *

UNITED STATES PATENT AND TRADEMARK OFFICE
CERTIFICATE OF CORRECTION

PATENT NO. : 4,801,597

DATED : January 31, 1989

INVENTOR(S) : Peter W. Stacpoole; Nicholas S. Bodor

It is certified that error appears in the above-identified patent and that said Letters Patent is hereby corrected as shown below:

Claim 6, column 12, line 2, after "claim 4", insert --in admixture with a--.

Signed and Sealed this

Twenty-fourth Day of October, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.   : 4,801,597
DATED        : January 31, 1989
INVENTOR(S)  : Peter W. STACPOOLE, ET AL It is certified that error appears in the above-identified patent and that said Letters Patent is hereby corrected as shown below:

On the Title page and in Col. 1, fourth line thereof,
    delete "MEUITUS" and substitute -- MELLITUS --.

Signed and Sealed this

Eighteenth Day of May, 1993

Attest:

MICHAEL K. KIRK

Attesting Officer  Acting Commissioner of Patents and Trademarks